United States Patent
Beller et al.

(10) Patent No.: US 9,066,723 B2
(45) Date of Patent: Jun. 30, 2015

(54) BIPOLAR CLAMP FOR HF SURGERY

(75) Inventors: Jürgen Beller, Gomaringen (DE);
Achim Brodbeck, Metzingen (DE);
Jürgen Hiller, Dettingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1233 days.

(21) Appl. No.: 12/988,085

(22) PCT Filed: Mar. 23, 2009

(86) PCT No.: PCT/EP2009/002117
§ 371 (c)(1),
(2), (4) Date: Nov. 12, 2010

(87) PCT Pub. No.: WO2009/127314
PCT Pub. Date: Oct. 22, 2009

(65) Prior Publication Data
US 2011/0066150 A1    Mar. 17, 2011

(30) Foreign Application Priority Data
Apr. 17, 2008    (DE) .......................... 10 2008 019 380

(51) Int. Cl.
*A61B 18/18* (2006.01)
*A61B 18/14* (2006.01)
*A61B 18/00* (2006.01)

(52) U.S. Cl.
CPC ......... *A61B 18/1477* (2013.01); *A61B 18/1445* (2013.01); *A61B 2018/00083* (2013.01)

(58) Field of Classification Search
CPC ........... A61B 18/1477; A61B 18/1445; A61B 2018/00083
USPC ...................................... 606/41–52
See application file for complete search history.

(56) References Cited

U.S. PATENT DOCUMENTS

| | | | |
|---|---|---|---|
| 6,162,220 A * | 12/2000 | Nezhat ............................ 606/48 |
| 8,568,444 B2 * | 10/2013 | Cunningham ................ 606/205 |
| 2002/0013583 A1 | 1/2002 | Camran et al. |
| 2002/0062123 A1 * | 5/2002 | McClurken et al. ............ 606/34 |
| 2003/0125729 A1 * | 7/2003 | Hooven et al. ................. 606/41 |
| 2006/0064086 A1 | 3/2006 | Odom |

FOREIGN PATENT DOCUMENTS

| | | |
|---|---|---|
| DE | 699 35 139 T2 | 10/2007 |
| EP | 0 875 209 B1 | 5/2006 |
| JP | H09-262245 A | 10/1997 |
| JP | 10-314180 A | 12/1998 |

(Continued)

*Primary Examiner* — Joseph Stoklosa
*Assistant Examiner* — Amanda Scott
(74) *Attorney, Agent, or Firm* — Dickstein Shapiro LLP

(57) ABSTRACT

A bipolar clamp for high-frequency surgery, in particular for coagulating tissue, having at least two bipolar clamping parts which are movable relative to one another, defining a grasping region between an open position and a coagulation position (e.g., closed position) and having electrodes for coagulating tissue that is grasped by the clamping parts in the grasping region. The clamping parts are formed of an electrically conductive core which is surrounded by a thin-layer electrical insulation and the electrodes are arranged on the clamping parts as thin pin electrodes that protrude through the thin-layer electrical insulation into the grasping region.

17 Claims, 3 Drawing Sheets

(56) References Cited

FOREIGN PATENT DOCUMENTS

| JP | 2002-513623 A | 5/2002 |
|----|---------------|--------|
| JP | 2008-000582 A | 1/2008 |
| WO | WO 97/17033 A2 | 5/1997 |
| WO | WO 99/56650 A1 | 11/1999 |
| WO | WO 01/22896 A1 | 4/2001 |
| WO | WO 2004/082495 A1 | 9/2004 |

* cited by examiner

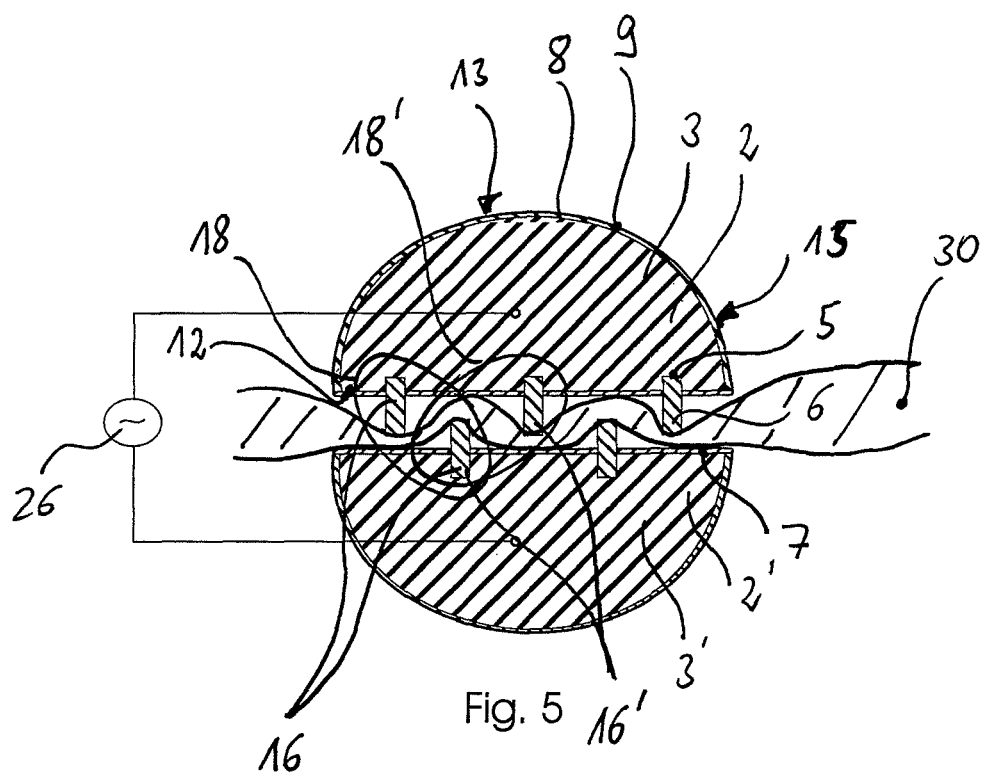

BIPOLAR CLAMP FOR HF SURGERY

FIELD OF THE DISCLOSED EMBODIMENTS

The disclosed embodiments relate to a bipolar clamp for high-frequency ("HF") surgery, in particular for coagulating tissue, having at least two bipolar clamping parts which are movable relative to one another between an open position and a coagulation position, defining a grasping region, and have electrodes for coagulating tissue grasped by the clamping parts in the grasping region.

BACKGROUND

High-frequency surgery has been used for many years in both human and veterinary medicine to coagulate and/or cut biological tissue. With the aid of suitable electrosurgical instruments, high-frequency current is passed through the tissue to be treated so that said tissue becomes changed due to protein coagulation and dehydration. The tissue contracts such that the vessels become closed and bleeding is stopped. A possible subsequent increase in current density can cause explosive evaporation of the tissue fluid and rupturing of the cell membranes, so that the tissue is completely parted.

For the thermal treatment of biological tissue, both bipolar and monopolar techniques are employed. In monopolar arrangements, the HF current fed by an HF generator to the electrosurgical instrument is applied via a 'different' electrode, while the current path through the body of a patient leads to an 'indifferent' neutral electrode and from there back to the HF generator.

However, bipolar instruments, which are configured with two electrode portions that are electrically insulated from one another, are becoming increasingly more important. The current path between the electrode portions is calculable and does not lead via extended routes through the body of the patient. This reduces the influence on heart pacemakers or other equipment that may be connected to the patient during the operation.

Bipolar instruments of this type are generally configured as clamping forceps which usually comprise, at their distal end, two clamping parts, which can be moved toward one another via an associated actuating device to grasp a tissue. In a clamping position or a "coagulation position," current flows from one clamping part, through the tissue, to the other clamping part, so that tissue grasped between the clamping parts can be treated by HF surgical means.

In the case of bipolar clamps for thermofusion or coagulation, used for example, during hysterectomy, when large volumes of tissue are grasped, the attempt is made to ensure that the emission of heat energy for coagulation is essentially limited to the region between the grasping surfaces of the clamping parts. In this way, undesirable heating of other sites (e.g., lateral thermal damage, heating with coagulation effects at the back of the jaws) is minimized. Particularly in the case of thin, small volume structures (e.g. parenchyma tissue, exposed blood vessels, etc.), the output of precisely dosed heat energy is also necessary, and this can only be ensured if the tissue volume during coagulation remains securely grasped and is not appreciably increased by involving additional material, e.g. due to thermal shrinkage.

A device for HF surgery is disclosed by EP 0 875 209 B1. What is described is a pair of clamping forceps for tissue coagulation, having, at the distal end thereof, two clamping parts joined to one another and movable relative to one another via an articulated connection. The two clamping parts delimit a grasping region in which the tissue to be treated can be firmly clamped. In order to enable particularly effective fixing of the tissue in the grasping region, one clamping part has movable fixing elements, which are movable into and out of the clamping part. Arranged at the other clamping part are two bipolar electrodes which are separated from one another by an electrical insulation layer. The first electrode protrudes out of this clamping part, while the second electrode surrounds this first electrode, being essentially laterally recessed. As soon as tissue is grasped between the two clamping parts and the HF generator is activated for coagulation current generation, current flows between the first protruding electrode, the grasped tissue, and the second electrode, wherein the coagulation process takes place in the tissue.

Disadvantageously, it has herein been found that, in this device, the whole clamping part heats up during the coagulation, resulting, inter alia, in undesirable vessel changes, such as spurious coagulation in the lateral and rear regions of the clamping part.

WO 2004-082495 A1 also discloses a bipolar clamp of this type for HF surgery, wherein two clamping parts are provided which are joined to one another into a jaw part for grasping the tissue to be coagulated. As before, the bipolar electrodes are arranged at one clamping part such that, following grasping of the tissue, current flows between the first electrode and the second electrode. The electrodes are configured as platform-like elevations, wherein the first electrode is arranged in the center and the second electrode is arranged as a ring-electrode surrounding the first electrode at the edge of the platform. In this case also, however, it has been found that due to a reduction in the conducting away of heat, heating of the clamping part carrying the electrodes cannot be prevented, so that undesirable tissue changes also take place in the side and rear region of the clamping part. Such a configuration can also only be realized with high cost and, due to the small bipolar electrode separations, is highly prone to faults in production.

US 2002/0013583 A1 also discloses a clamp for HF surgery, wherein, inter alia, the bipolar electrodes are provided on different clamping parts, so that a current flows between one electrode of one clamping part and another electrode of the other clamping part. In this case, the electrodes are laid on conducting paths which are arranged, in particular, on clamping surfaces of the clamping parts which face one another. The electrodes themselves are configured as electrode tips and are constructed so that, on grasping the tissue, they penetrate into the tissue to be coagulated. The intention of this is that the coagulation areas can be more precisely delineated by the individual bipolar electrodes penetrating the tissue. However, it has here again been found that heating of the tissue takes place in the side and rear regions of the clamping parts and that this heating is the cause of undesirable tissue changes in these regions. Furthermore, the production of such clamping parts involves technical manufacturing difficulties, since the fixing of the electrodes to the clamping part may not be able to withstand the very great mechanical and thermal loading.

SUMMARY

The disclosed embodiments provide a bipolar clamp for HF surgery which enables much more precise alignment of the coagulation areas and, in particular, prevents undesirable coagulation of adjacent tissue, and which can be produced more easily and economically and with fewer errors.

In particular, one disclosed embodiment includes a bipolar clamp for HF surgery, in particular for coagulating tissue, having at least two bipolar clamping parts which are movable relative to one another, defining a grasping region between an open position and a coagulation position (e.g. closed position) and having electrodes for coagulating tissue grasped by the clamping parts in the grasping region. The clamping parts essentially entirely comprise an electrically conductive core which is surrounded by a thin-layer of electrical insulation, wherein the electrodes are arranged on the core as pin electrodes and protrude through the thin electrical insulation layer in the grasping region.

In this context, the expression 'thin layer' should be understood to mean a layer the mass of which and, in particular, the effect of which is essentially negligible due to having a very small thickness in direct comparison with the mass of the electrically conductive core of each clamping part. The thin layer in question also contributes nothing to the stability of the clamping parts and assumes no supporting function. For this reason, the core of each clamping part can be very easily, quickly and inexpensively provided with a thin layer of this type for electrical insulation, for example, by means of a dipping bath or spray treatment.

At the core of the disclosed embodiments is that, due to the clamping parts essentially entirely comprising an electrically conducting core and surrounded by a thin electrical insulation layer, heating of said clamping parts is prevented by means of the very thin pin electrodes arranged on the cores. Since the electrodes protrude as thin pins from the very massive cores of the clamping parts, heat which is produced at the electrodes during the coagulation is effectively conducted away without any appreciable heating of the clamping parts.

A further essential point is that the thermal relaxation time, that is, the time that each electrode requires to reach thermal equilibrium with the core and, naturally, the surroundings is very short.

Apart from reducing heating of the clamping parts and therefore the undesirable coagulation of tissue that lies, for example, against the rear of the clamping part, the arrangement of the electrodes according to the invention leads also to a reduction in the influence of thermal shrinkage on the tissue volume.

Preferably, the ratio of heat capacities of all the electrodes to the heat capacity of the core is designed to be so small that during coagulation, heating of the clamping parts is essentially prevented. This effect is also achieved because the total volume of the electrodes is much smaller than the total volume of the electrically conductive cores. A clamping part configured in this way provides benefits of much quicker heating of the electrodes and, above all, of much quicker cooling, without heating up the core, and thus without heating up the clamping part.

Preferably, the total surface area of the electrodes is selected to be much smaller than the total surface area of the clamping parts. Apart from the indirectly resulting improved heat removal, this arrangement also results in increased current density at the very small electrode surfaces relative to a very broad electrode, as known from the prior art. This leads to more rapid heating, which in turn reduces the undesirable heating of the core and the clamping part.

Preferably, the electrodes have a flattened form at the free end thereof such that penetration of said electrodes into the grasped tissue in the coagulation position is substantially prevented. The result is a reduction in the mechanical damage to tissue in the grasping region, while the advantage of dedicated coagulation areas can nevertheless be used. For this purpose, the electrodes are preferably configured cylindrically. Naturally, other forms, particularly rotationally symmetrical forms, of electrodes can be selected, provided penetration into the tissue is essentially prevented. It is preferred that the electrodes be arranged orthogonally to the clamping part surfaces of the clamping parts which face toward the grasping region, at least at the base of said electrodes (e.g., the region at which said electrodes are arranged on the core).

Preferably, the electrodes are configured integrally with the core. In this way, it is possible, for example, to manufacture the core together with the electrodes in a single operation and thereby further reduce the production costs. This method of production also ensures a highly stable and robust electrode seating and therefore results in a very robust clamping part.

However, it is also possible to arrange the electrodes in complementary electrode receptacles on the core, so that they are inserted, for example, after production of the core and can be adapted to particular requirements. In this case, the design of such individual 'adaptable' electrodes is also possible. Additionally, spacers, clamping elements, mechanical cutting protrusions, etc., can also be inserted into suitable electrode receptacles, either insulated or non-insulated.

The electrodes are preferably arranged on the cores or the clamping parts, spaced apart and offset from one another, in each case leaving an intermediate space, such that in the coagulation position, the electrodes of one clamping part are partially immersed in the intermediate spaces formed by the electrodes of the other clamping part. Therefore, in this 'sawtooth configuration,' coagulation current flows in the coagulation position essentially horizontally to the clamping part surfaces of the clamping parts, between the electrodes which are partially immersed, relative to one another, into the corresponding intermediate spaces. In this way, the coagulation areas formed between the respective bipolar electrodes are spatially limited.

Preferably, the electrodes are arranged such that, in the coagulation position, the current producing a coagulation area flows between the electrodes forming an intermediate space and an electrode immersed into this intermediate space. The electrodes are preferably spaced apart from one another such that said coagulation areas at least partially overlap. This contributes decisively to a spatially limited but very effective local coagulation.

Preferably, in order to achieve even coagulation, the intermediate spaces of a plurality of the individual electrodes are approximately identical. Preferably, this naturally also means that the distances between the electrodes bordering the intermediate spaces and the electrodes immersed into said intermediate spaces are approximately identical. The electrodes on the clamping parts or cores can be arranged in a plurality of parallel or non-parallel columns, in a plurality of corresponding rows, or arbitrarily.

Preferably, the thin-layer insulation is configured as an insulation plate on the clamping part surfaces of the core and as an insulation coating on the remainder of the core surface. This offers the possibility, particularly on use of electrodes subsequently arranged on the clamping part, of completely insulating cores which are prefabricated and partially insulated by the insulation coating, after mounting the electrodes by pushing on the insulation plate over the protruding electrodes.

Most known electrically insulating and thermoresistant materials, particularly those known for use with HF surgery, are usable for the insulation, provided they can be applied as thin-layer coatings and meet the relevant medical requirements.

The bipolar clamp preferably has arms that are connected to one another via an articulated connection and have proximal actuating devices for opening and closing the clamp parts arranged distally on the arms, wherein the electrodes are each pivoted round the articulated connection following a circular path on which said electrodes move during opening and closing of the clamping parts.

Particularly when the arms are arranged in the form of a pair of forceps or scissors, for example a scissor-like or forceps-like surgical instrument, the electrodes protruding from the core move in a circular path round the articulated connection. If the electrodes of one clamping part enter the intermediate spaces formed by the electrodes of the other clamping part, it is ensured by the individual electrodes pivoted according to the circular path, that the separations of the electrodes immersing relative to one another remain constant over the whole electrode length, so that an even flow of current between the individual electrodes is ensured.

Preferably, the length of the electrodes protruding from at least one core increases, particularly in proportion to the respective distance from the articulated connection. In this way, it is ensured that, shortly before reaching the coagulation position, seen over the length of the clamping parts, the individual electrodes essentially all immerse simultaneously into the respective intermediate spaces.

BRIEF DESCRIPTION OF THE DRAWINGS

The disclosed embodiments will now be described in greater detail, pointing out further features and advantages by reference to exemplary embodiments as illustrated in the drawings.

FIG. 5 is a cross-sectional view through a second embodiment of a bipolar clamp.

DETAILED DESCRIPTION

In the following, the same reference signs are used for the same and similarly acting components, wherein for differentiation, primes are occasionally used.

Figure 1:
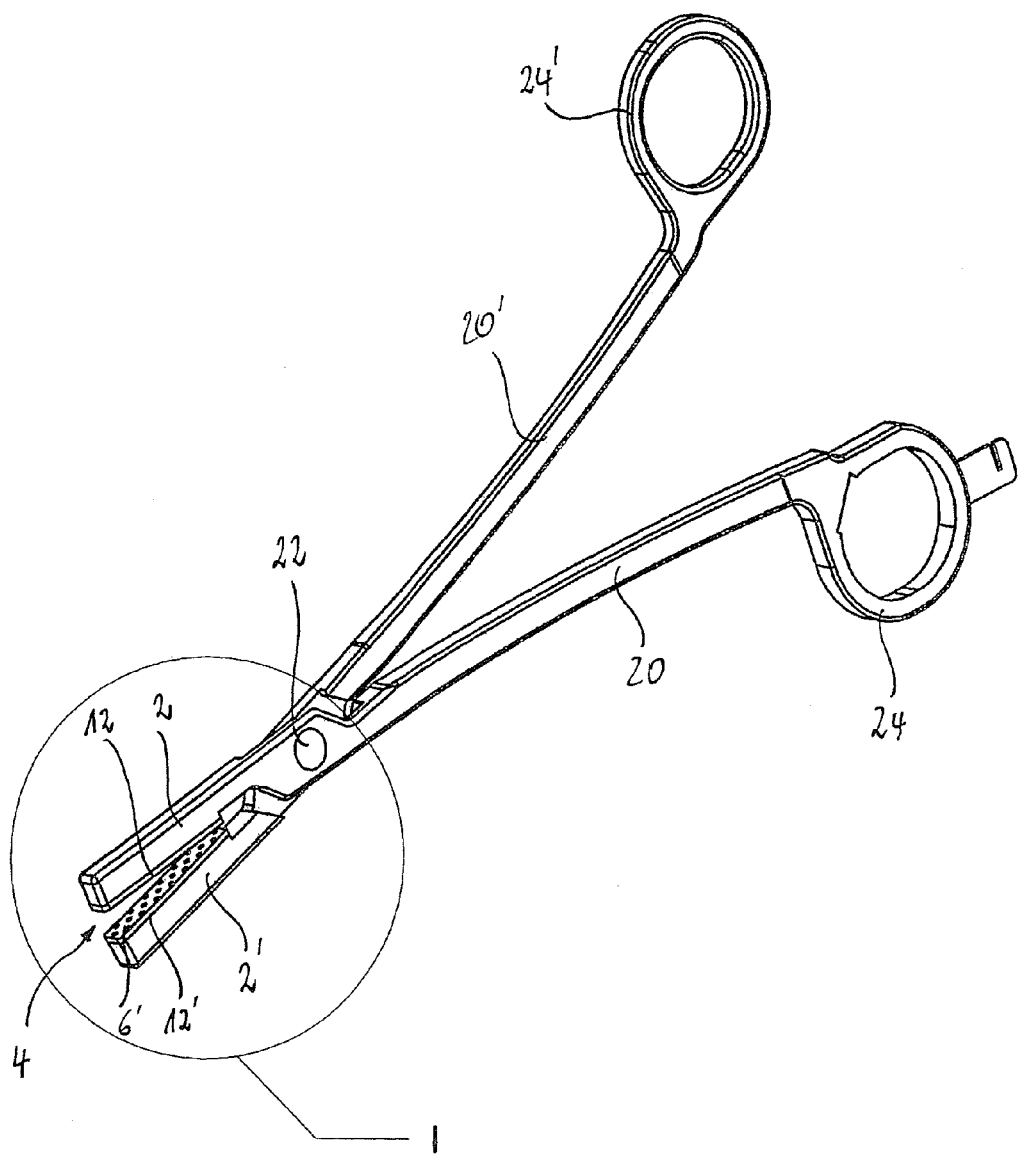
FIG. 1 is an isometric representation of an HF surgical device including a first embodiment of the bipolar clamp.

FIG. 1 shows an isometric representation of an HF surgical instrument. The surgical instrument comprises two arms 20, 20' which are connected to one another via an articulated connection 22 in the form of a pair of forceps or scissors such that two clamping parts 2, 2' arranged at the distal end of the arms 20, 20' can be moved from an open position into a closed position and vice versa. Also provided at the proximal end of the arms are two actuating devices 24, 24', e.g., in the form of handles, which enable the opening and closing of the arms 20, 20' and thus also the opening and closing of the clamping parts 2, 2'.

The clamping parts 2, 2' together form a grasping region 4 in which tissue to be coagulated (or similarly HF surgically treated (see FIG. 5)) can be grasped. In order to carry out the HF surgical operation, electrodes 6, 6' are arranged at the clamping parts 2, 2', and particularly at the clamping part surfaces 12, 12' facing toward the grasping region 4. The electrodes may be placed at different polarities by means of an HF generator (not shown) connected via the arms 20, 20'. As soon as tissue is grasped in the grasping region 4 by the clamping parts 2, 2', and particularly by the electrodes 6, 6', following activation of the HF generator, a current (used for coagulation or similar HF surgical processes) flows between the clamping parts 2, 2' and the electrodes 6, 6' arranged thereon.

Figure 2:
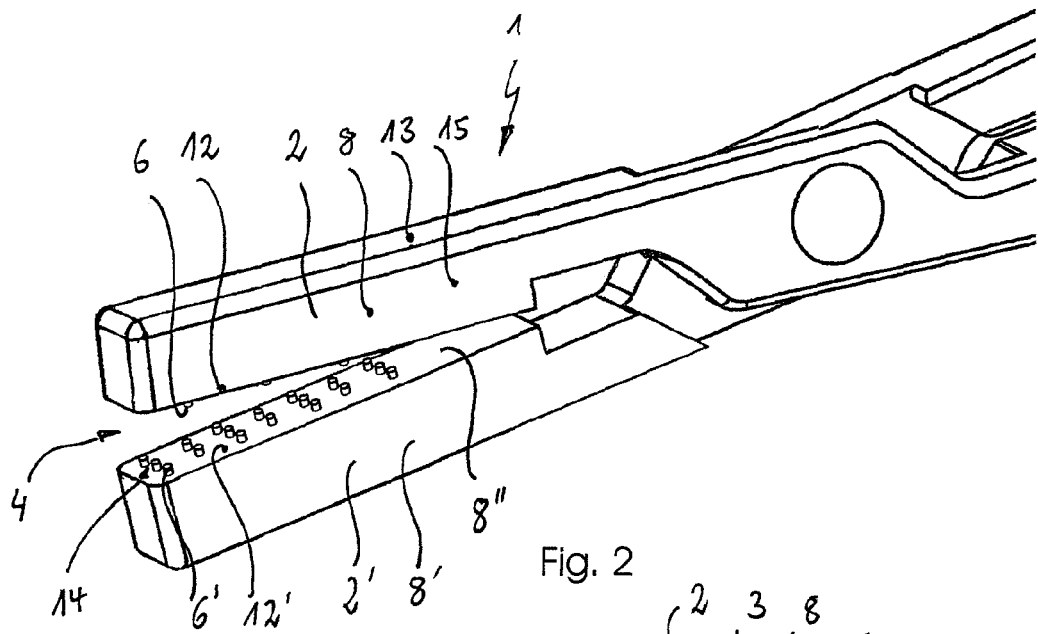
FIG. 2 is a detailed representation of the bipolar clamp according to the embodiment of FIG. 1.

FIG. 2 shows the bipolar clamp 1 of the embodiment of FIG. 1, formed by the two clamping parts 2, 2', in more detail. Clearly illustrated, protruding orthogonally out of the clamping part surfaces 12, 12', are the electrodes 6, 6', which are designed cylindrically as thin pin electrodes and arranged at a particular distance 14 from one another. In this embodiment, the electrodes 6, 6' are arranged along the clamping parts 2, 2' in alternating rows of two and three. Naturally, other electrode arrangements can also be selected.

As soon as tissue is grasped in the grasping region 4 of the two clamping parts 2, 2', current is applied to the tissue via the electrodes 6, 6' and the desired HF surgical operation is performed. In this embodiment, the clamping parts 2, 2' are completely surrounded by a thin-layer electrical insulation 8, so that an undesirable flow of current between non-insulated parts of the clamping parts 2, 2' is prevented.

Figure 3:
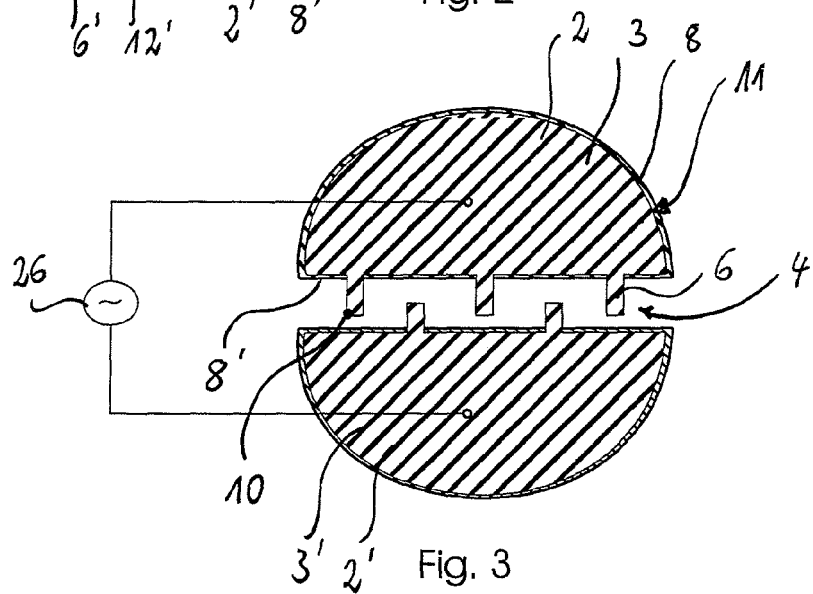
FIG. 3 is a cross-section view through the bipolar clamp of FIG. 2.

In order to avoid undesirable heating, particularly of the clamping part rear 13 and the clamping part sides 15, according to the disclosed embodiments, the clamping parts 2 entirely comprise a conductive core 3, 3' (see FIGS. 3 and 5). In the example embodiment shown here, the electrodes 6, 6' are configured integrally with said conductive core 3, 3' (see, in particular, FIG. 3). It is clear that the total of the heat capacities of the electrodes 6, 6' of a clamping part 2, 2' is much smaller than the heat capacity of the clamping part 2, 2' or the core 3, 3' thereof, so that during coagulation or a similar HF operation, no appreciable heating of the clamping part 2, 2' is seen.

Due to the size and mass differences, the thin electrodes 6, 6' heat up very rapidly, while the core 3, 3' heats up slowly due to the large mass thereof.

The same takes place after completion of the HF operation: the electrodes 6, 6' which are small in comparison with the core 3, 3' cool down to the ambient temperature much quicker and undesired coagulation is avoided.

In addition, due to the very large conductive surface of the core 3, 3', heating induced by the flow of current does not occur; it is only at the electrodes 6 that the temperature rises rapidly, so that thermal treatments can be carried out rapidly and in a spatially limited manner.

Apart from reducing heating and, thus also reducing the unwanted coagulation of tissue, the embodiment of the clamping parts 2, 2' and the whole surgical instrument also leads to a reduction in the influence of thermal shrinkage on tissue volume.

The electrodes 6, 6' have a flattened region at their free end 10, such that they do not penetrate into the tissue grasped in the grasping region 4. This prevents mechanical damage to the tissue.

In order to prevent coagulation in other regions than in the electrode regions, each core 3, 3' of each clamping part 2, 2' is surrounded by a thin-layer insulation 8 for electrical insulation. In this embodiment, this thin-layer insulation 8 is distributed over the core 2, 2' on the whole surface and is applied, in particular, in the form of a dip coating onto the core surface 11, wherein only the electrodes 6, 6' protrude uninsulated out of the thin-layer insulation 8 into the grasping region 4. It should be noted here that it is also possible to insulate the electrodes 6, 6' partly with a thin layer 8 and, for example, to leave only the free ends 10 uninsulated.

Shown schematically in FIG. 3 is the connection of the high frequency generator 26 which is electrically connected to each core 3, 3' of the clamping parts 2, 2' such that said generator 26 can place said core 3, 3' at different potentials during the coagulation.

Figure 4:
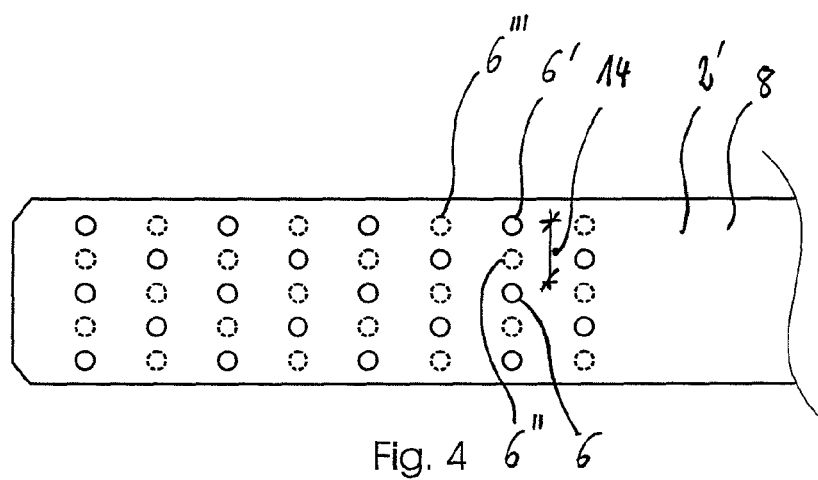
FIG. 4 is a longitudinal section through the bipolar clamp of FIG. 2.

FIG. 4 shows the embodiment of FIG. 3 in a plan view or a longitudinal section in the coagulation position, that is, with the clamping parts 2, 2' basically closed and with the electrodes 6, 6' immersed relative to one another. Also shown are both the electrodes 6, 6' of the clamping part 2' as well as the electrodes 6", 6'" which are arranged on the other clamping part 2 (see FIG. 2) and here are immersed in the electrode intermediate space 14 at the clamping part 2'.

The offset arrangement of the electrodes is visible in FIGS. 3 and 4. All the electrodes are arranged on the respective clamping parts 2 such that two electrodes 6', 6 form an intermediate space 14 in each case, into which an electrode 6" of the other clamping part 2' (see, in particular, FIG. 3) is immersed.

In this embodiment, the electrodes are arranged such that the distance between the immersed electrode 6" and the two electrodes 6, 6' delimiting the intermediate space 14 is equal. Naturally, in place of the even distribution of the electrodes shown, it is also possible to arrange the electrodes offset by columns or rows, so that, for example, an immersed electrode of a clamping part is simultaneously enclosed by three electrodes of the other clamping part which delimit an intermediate space 14.

FIG. 5 shows another embodiment of the bipolar clamp 2 in a cross-section similar to FIG. 3. However, in this case, the electrodes 6 are not integrally bound to the core 3, 3', but are each accommodated in electrode receptacles 5 formed in the respective cores 3, 3'. In this embodiment, is therefore possible either to press the electrodes 6 into the electrode receptacles 5, to cement said electrodes 6 in an electrically conducting manner or to fix said electrodes 3 in like manner. In place of electrodes 6, other elements, such as spacing elements, fixing elements, etc. can also be accommodated by the electrode receptacles 5 and fastened to the core.

As in the previous embodiment, the tissue 30 to be treated by coagulation or similar HF surgical technique is grasped between the two clamping parts 2, 2' in the grasping region 4. As soon as current is applied to the clamping parts 2, 2' or the cores 3, 3' via the HF generator 26, spatially limited coagulation areas 18, 18' form between bipolar electrode pairs 16, 16' of different clamping parts 2. In the embodiment according to FIG. 5, the electrodes 6 are arranged such that the coagulation areas 18, 18' thereby formed at least partially overlap.

In this embodiment, the thin-layer insulation 8 is also configured as a two-part thin layer. Said thin layer comprises a thin-layer electrical insulation coating 9, which surrounds the cores 3, 3' on the side and rear regions 13, 15, and also an electrical insulation plate 7, which is arranged on the clamping part surfaces 12 and is penetrated by the electrodes 6.

It should be noted at this point that all the aforementioned parts are claimed as essential to the invention both alone and in any combination, particularly the details shown in the drawings. Amendments thereof are the common practice of persons skilled in the art.

The invention claimed is:

1. A bipolar clamp for use in high-frequency surgery, in particular for coagulation of tissue, the bipolar clamp comprising:
at least two bipolar clamping parts movable relative to one another, between an open position and a coagulation position, and in the coagulation position the clamping parts define a grasping region, and configured to grasp tissue in the grasping region, each clamping part comprising:
an electrically conductive core;
a thin-layer electrical insulation surrounding the electrically conductive core; and
a plurality of electrodes configured to coagulate the tissue, arranged as pin electrodes on the electrically conductive core and protruding through the thin-layer electrical insulation into the grasping region,
wherein each clamping part is made substantially completely of the respective electrically conductive core, and
wherein a ratio of heat capacities of all the electrodes on a particular electrically conductive core to a heat capacity of the particular electrically conductive core is such that during operation, heating of the clamping parts is substantially prevented.

2. The bipolar clamp according to claim 1, wherein the high-frequency surgery comprises coagulating tissue.

3. The bipolar clamp according to claim 1, wherein each electrode has a flattened surface at a free end thereof such that penetration of said electrode into tissue grasped in the grasping region when the clamping parts are in the coagulation position is substantially prevented.

4. The bipolar clamp according to claim 1, wherein the electrodes have a cylindrical form.

5. The bipolar clamp according to claim 1, wherein the electrodes are configured integrally with the respective electrically conductive core.

6. The bipolar clamp according to claim 1, wherein the electrodes are arranged in complementary electrode receptacles on the respective electrically conductive core.

7. The bipolar clamp according to claim 1, wherein the electrodes are arranged on the respective electrically conductive cores such that the electrodes are orthogonal to clamping part surfaces of the clamping parts which face toward the grasping region.

8. The bipolar clamp according to claim 1, wherein the electrodes are arranged on the respective electrically conductive cores such that the electrodes are spaced apart and offset from one another, in each case leaving an intermediate space, such that in the coagulation position, the electrodes of one clamping part are at least partially immersed in the intermediate spaces formed by the electrodes of the other clamping part.

9. The bipolar clamp according to claim 8, wherein the electrodes are arranged and configured such that when tissue is grasped in the grasping region when the clamping parts are in the coagulation position, a current flows between the electrodes of one clamping part forming an intermediate space and the electrode of the other clamping part immersed into the intermediate space, thereby producing a coagulation area.

10. The bipolar clamp according to claim 9, wherein the electrodes are spaced apart from one another such that the coagulation areas formed by the current flow between the respective electrodes forming coagulation pairs at least partially overlap.

11. The bipolar clamp according to claim 8, wherein a plurality of intermediate spaces is formed, each of the plurality of intermediate spaces being substantially identical.

12. The bipolar clamp according to claim 1, wherein the thin-layer electrical insulation is configured as an insulation plate on clamping part surfaces of the clamping parts which face toward the grasping region and as an insulation coating on a remainder of a surface of the electrically conductive core.

13. The bipolar clamp according to claim 1, further comprising arms having the clamping parts arranged distally on the arms, the arms being connected together via an articulated connection and have proximal actuating devices for opening and closing the clamping parts arranged distally thereon, wherein the respective electrodes are each pivoted round the articulated connection following a circular path on which said electrodes move during opening and closing of the clamping parts.

14. The bipolar clamp according to claim 13, wherein lengths of the electrodes protruding from at least one electrically conductive core increase in proportion to a distance from the articulated connection.

15. A surgical instrument for high-frequency surgery, comprising:
   at least one bipolar clamp according to claim 1;
   at least two arms, connected to one another via an articulated connection; and
   proximal actuating devices for opening and closing the clamping parts of the at least one bipolar clamp which are arranged distally on the arms.

16. A bipolar clamp for use in high-frequency surgery, in particular for coagulation of tissue, the bipolar clamp comprising:
   at least two bipolar clamping parts movable relative to one another, between an open position and a coagulation position, and in the coagulation position the clamping parts define a grasping region, and configured to grasp tissue in the grasping region, each clamping part comprising:
      an electrically conductive core;
      a thin-layer electrical insulation surrounding the electrically conductive core; and
      a plurality of electrodes configured to coagulate the tissue, arranged as pin electrodes on the electrically conductive core and protruding through the thin-layer electrical insulation into the grasping region,
   wherein each clamping part is made substantially completely of the respective electrically conductive core, and
   wherein a total volume of the electrodes on a particular electrically conductive core is smaller than a total volume of the particular electrically conductive core.

17. A bipolar clamp for use in high-frequency surgery, in particular for coagulation of tissue, the bipolar clamp comprising:
   at least two bipolar clamping parts movable relative to one another, between an open position and a coagulation position, and in the coagulation position the clamping parts define a grasping region, and configured to grasp tissue in the grasping region, each clamping part comprising:
      an electrically conductive core;
      a thin-layer electrical insulation surrounding the electrically conductive core; and
      a plurality of electrodes configured to coagulate the tissue, arranged as pin electrodes on the electrically conductive core and protruding through the thin-layer electrical insulation into the grasping region,
   wherein each clamping part is made substantially completely of the respective electrically conductive core, and
   wherein a total surface area of the electrodes on a particular electrically conductive core is smaller than a total surface area of the respective clamping part.

* * * * *